US010702003B2

(12) United States Patent
Patel et al.

(10) Patent No.: US 10,702,003 B2
(45) Date of Patent: Jul. 7, 2020

(54) APPARATUS FOR REDUCING ANGULAR VELOCITY OF PROTECTIVE SHELLS ASSOCIATED WITH PROTECTIVE HEADWEAR

(71) Applicant: ILLINOIS TOOL WORKS, INC., Glenview, IL (US)

(72) Inventors: Nishank R. Patel, Appleton, WI (US); Eric T. Sommers, Appleton, WI (US); Kyle Pfeifer, Appleton, WI (US)

(73) Assignee: ILLINOIS TOOL WORKS INC., Glenview, IL (US)

( * ) Notice: Subject to any disclaimer, the term of this patent is extended or adjusted under 35 U.S.C. 154(b) by 0 days.

(21) Appl. No.: 14/962,296

(22) Filed: Dec. 8, 2015

(65) Prior Publication Data

US 2016/0183622 A1  Jun. 30, 2016

Related U.S. Application Data

(60) Provisional application No. 62/096,948, filed on Dec. 26, 2014.

(51) Int. Cl.
  *A42B 3/22* (2006.01)
  *A61F 9/06* (2006.01)

(52) U.S. Cl.
  CPC .............. *A42B 3/222* (2013.01); *A42B 3/225* (2013.01); *A61F 9/06* (2013.01)

(58) Field of Classification Search
  CPC ............ A42B 3/222; A42B 3/225; A61F 9/06
  See application file for complete search history.

(56) References Cited

U.S. PATENT DOCUMENTS

| 1,182,367 | A | 5/1916 | Gravell |
| 1,338,022 | A | 4/1920 | Lamoreaux |
| 1,601,830 | A | 10/1926 | Huntsman |
| 1,994,103 | A | 3/1935 | Huey |
| 2,169,745 | A | 8/1939 | Shipman |
| 2,194,492 | A | 3/1940 | Bowers |
| 2,402,820 | A | 6/1946 | Kitchen |
| 2,411,831 | A | 11/1946 | Lehmberg et al. |

(Continued)

FOREIGN PATENT DOCUMENTS

| CA | 2436816 A1 | 3/2004 |
| CN | 101056677 A | 10/2007 |

(Continued)

OTHER PUBLICATIONS

International Search Report and Written Opinion for PCT/US2015/065213 dated Mar. 16, 2016, 13 pages.

(Continued)

*Primary Examiner* — Megan E Lynch
(74) *Attorney, Agent, or Firm* — Klintworth & Rozenblat IP LLP

(57) ABSTRACT

In one aspect, a protective headwear is provided and includes a support member configured to engage a user's head, an outer shell coupled to the support member and rotatable relative to the support member between a first position and a second position, and a member coupled between the support member and the outer shell to reduce angular velocity of the outer shell as it moves from the first position to the second position. In one aspect, the protective headwear is a welding helmet.

30 Claims, 11 Drawing Sheets

(56) References Cited

U.S. PATENT DOCUMENTS

| | | |
|---|---|---|
| 2,487,848 A | 11/1949 | Bowers |
| 2,658,200 A | 11/1953 | Bowers, Sr. |
| 2,700,158 A | 1/1955 | Larsen |
| 2,763,006 A | 9/1956 | Amundsen |
| 3,074,072 A | 1/1963 | Edwards et al. |
| 3,112,745 A | 12/1963 | Boyer |
| 3,214,768 A | 11/1965 | Bohner |
| 3,430,263 A | 3/1969 | Newcomb |
| 3,609,765 A | 10/1971 | Molitoris |
| 3,696,442 A | 10/1972 | Amundsen |
| 3,868,727 A | 3/1975 | Paschall |
| 3,881,478 A | 5/1975 | Rosendahl |
| 4,040,123 A * | 8/1977 | Williams .............. A61F 9/06  2/10 |
| 4,080,664 A | 3/1978 | Morris et al. |
| 4,109,320 A | 8/1978 | Anderson |
| 4,335,472 A | 10/1982 | Wedge |
| D270,642 S | 9/1983 | Watts |
| 4,464,800 A * | 8/1984 | Edwards .............. A61F 9/06  2/451 |
| 4,479,738 A | 10/1984 | Kubnick |
| 4,499,630 A | 2/1985 | Harris |
| 4,793,001 A | 12/1988 | Accardi |
| 4,853,973 A | 8/1989 | Boochard |
| D316,020 S | 4/1991 | Fushiya |
| 5,003,632 A | 4/1991 | Claude |
| 5,012,528 A | 5/1991 | Pernicka |
| 5,040,528 A | 8/1991 | O'Neill |
| 5,044,019 A | 9/1991 | Shewchenko |
| 5,077,836 A | 1/1992 | Idoff et al. |
| D329,590 S | 9/1992 | Chapman |
| 5,386,592 A | 2/1995 | Checkeroski |
| 5,412,811 A | 5/1995 | Hildenbrand |
| D365,666 S | 12/1995 | Gumpp |
| 5,724,119 A | 3/1998 | Leight |
| D393,933 S | 4/1998 | Huh |
| 5,752,280 A | 5/1998 | Hill |
| D398,421 S | 9/1998 | Crafoord |
| D421,116 S | 2/2000 | Mattila |
| 6,035,451 A | 3/2000 | Burns et al. |
| 6,055,983 A | 5/2000 | Metzger |
| 6,102,033 A | 8/2000 | Baribeau |
| D433,751 S | 11/2000 | Reischel |
| 6,154,881 A | 12/2000 | Lee |
| 6,185,739 B1 | 2/2001 | Verkic et al. |
| 6,260,197 B1 * | 7/2001 | Hoogewind .......... A61F 9/061  2/8.3 |
| 6,264,392 B1 | 7/2001 | Wise |
| D449,103 S | 10/2001 | Legare |
| 6,341,382 B1 | 1/2002 | Ryvin et al. |
| 6,367,085 B1 | 4/2002 | Berg |
| 6,393,617 B1 | 5/2002 | Paris |
| D465,568 S | 11/2002 | Petherbridge |
| D467,489 S | 12/2002 | Rubinson |
| D489,492 S | 5/2004 | Wu |
| D492,559 S | 7/2004 | Itano |
| 6,782,558 B1 | 8/2004 | Keen, Sr. et al. |
| 6,973,672 B2 | 12/2005 | Huh |
| 6,973,676 B1 | 12/2005 | Simpson |
| D520,856 S | 5/2006 | Osiecki |
| D520,859 S | 5/2006 | Osiecki |
| D521,190 S | 5/2006 | Wu |
| 7,089,603 B2 | 8/2006 | Ketterer et al. |
| D530,185 S | 10/2006 | Osiecki |
| 7,120,939 B1 * | 10/2006 | Howard .............. A42B 3/14  2/416 |
| 7,178,932 B1 | 2/2007 | Buckman |
| D543,828 S | 6/2007 | Strutin-Belinoff |
| 7,284,281 B2 | 10/2007 | Huh |
| D557,128 S | 12/2007 | Sawdon |
| 7,308,719 B2 | 12/2007 | Huh |
| 7,441,282 B2 | 10/2008 | Heine |
| D584,003 S | 12/2008 | Juhlin |
| D589,654 S | 3/2009 | Juhlin |
| D589,776 S | 4/2009 | Camp |
| D590,232 S | 4/2009 | Demers |
| 7,534,005 B1 | 5/2009 | Buckman |
| D600,094 S | 9/2009 | Hwang |
| D602,639 S | 10/2009 | Ho |
| D617,459 S | 6/2010 | Bogue |
| D626,963 S | 11/2010 | Kim |
| D632,944 S | 2/2011 | Kang |
| D635,721 S | 4/2011 | Cheng |
| D654,224 S | 2/2012 | Wu |
| D654,634 S | 2/2012 | Wu |
| 8,214,920 B1 | 7/2012 | Edgar |
| D667,173 S | 9/2012 | Juhlin |
| 8,286,269 B2 | 10/2012 | Springer et al. |
| 8,336,114 B1 * | 12/2012 | Lee .............. A42B 3/145  2/9 |
| D674,150 S | 1/2013 | Juhlin |
| D674,153 S | 1/2013 | Daniels |
| D676,551 S | 2/2013 | Desai |
| 8,381,312 B2 | 2/2013 | Seo |
| D684,252 S | 6/2013 | Okada |
| D710,546 S | 8/2014 | Wu |
| 8,826,464 B2 | 9/2014 | Wu |
| D722,259 S | 2/2015 | Conner |
| 8,990,963 B2 | 3/2015 | Matthews |
| 9,038,198 B2 | 5/2015 | Feinberg |
| D735,949 S | 8/2015 | Dion |
| D735,951 S | 8/2015 | Birath |
| 9,125,448 B2 | 9/2015 | Klotz |
| 9,155,923 B2 | 10/2015 | Proctor |
| D742,596 S | 11/2015 | Peng |
| D743,629 S | 11/2015 | Peng |
| D747,556 S | 1/2016 | Fujita |
| D749,796 S | 2/2016 | Barmore |
| 9,427,040 B2 | 8/2016 | Leyland |
| D767,829 S | 9/2016 | Wu |
| 9,516,911 B2 | 12/2016 | Happel |
| 9,706,805 B2 | 7/2017 | Pereira |
| 9,956,118 B2 | 5/2018 | Sernfalt |
| 2003/0135911 A1 * | 7/2003 | Wang-Lee .............. A61F 9/064  2/169 |
| 2004/0179149 A1 | 9/2004 | Wang-Lee |
| 2006/0080761 A1 * | 4/2006 | Huh .............. A42B 3/04  2/424 |
| 2006/0225187 A1 | 10/2006 | Wu |
| 2007/0113318 A1 | 5/2007 | Weston |
| 2007/0220649 A1 * | 9/2007 | Huh .............. A61F 9/025  2/9 |
| 2007/0245467 A1 * | 10/2007 | Lilenthal .............. A42B 3/14  2/416 |
| 2008/0060102 A1 | 3/2008 | Matthews |
| 2009/0235420 A1 | 9/2009 | Chiang |
| 2010/0050325 A1 | 3/2010 | Wang-Lee |
| 2010/0212058 A1 | 8/2010 | Wanhainen |
| 2010/0229274 A1 * | 9/2010 | Ahlgren .............. A42B 3/225  2/8.2 |
| 2010/0229286 A1 | 9/2010 | Ahlgren |
| 2010/0235971 A1 | 9/2010 | Ahlgren |
| 2010/0287676 A1 | 11/2010 | Seo |
| 2011/0101890 A1 | 5/2011 | Robinson |
| 2011/0167542 A1 | 7/2011 | Bayne |
| 2011/0179541 A1 * | 7/2011 | Wright .............. A61F 9/064  2/12 |
| 2012/0144565 A1 * | 6/2012 | Huh .............. A61B 90/35  2/421 |
| 2012/0291172 A1 | 11/2012 | Wills |
| 2013/0111653 A1 | 5/2013 | Huh |
| 2014/0007312 A1 | 1/2014 | Wright |
| 2014/0208476 A1 | 7/2014 | Chen |
| 2014/0298557 A1 | 10/2014 | Townsend, Jr. |
| 2015/0143618 A1 | 5/2015 | Pereira et al. |
| 2015/0264992 A1 | 9/2015 | Happel |
| 2015/0359680 A1 | 12/2015 | Gardner |
| 2016/0081856 A1 | 3/2016 | Hofer-Kraner |
| 2016/0183622 A1 | 6/2016 | Patel |
| 2016/0360821 A1 | 12/2016 | Benton |
| 2017/0112226 A1 | 4/2017 | Watkins |

(56) References Cited

U.S. PATENT DOCUMENTS

FOREIGN PATENT DOCUMENTS

| | | | |
|---|---|---|---|
| CN | 101795645 A | 8/2010 |
| CN | 101815556 A | 8/2010 |
| CN | 101827538 A | 9/2010 |
| CN | 102370541 A | 3/2012 |
| CN | 102525731 A | 7/2012 |
| CN | 102551956 A | 7/2012 |
| CN | 203264074 U | 11/2013 |
| CN | 103653495 A | 3/2014 |
| EP | 2 907 401 A1 | 8/2015 |
| WO | 2008/025083 A1 | 3/2008 |
| WO | 2014160149 A2 | 10/2014 |
| WO | 2015195495 A1 | 12/2015 |

OTHER PUBLICATIONS

International Search Report and Written Opinion for PCT/US2015/035713 dated Oct. 27, 2015, 17 pages.
Communication pursuant to Rule 94(3) EPC issued for EP 15 7 2 8 713.7 dated Jul. 11, 2018, 5 pages.

* cited by examiner

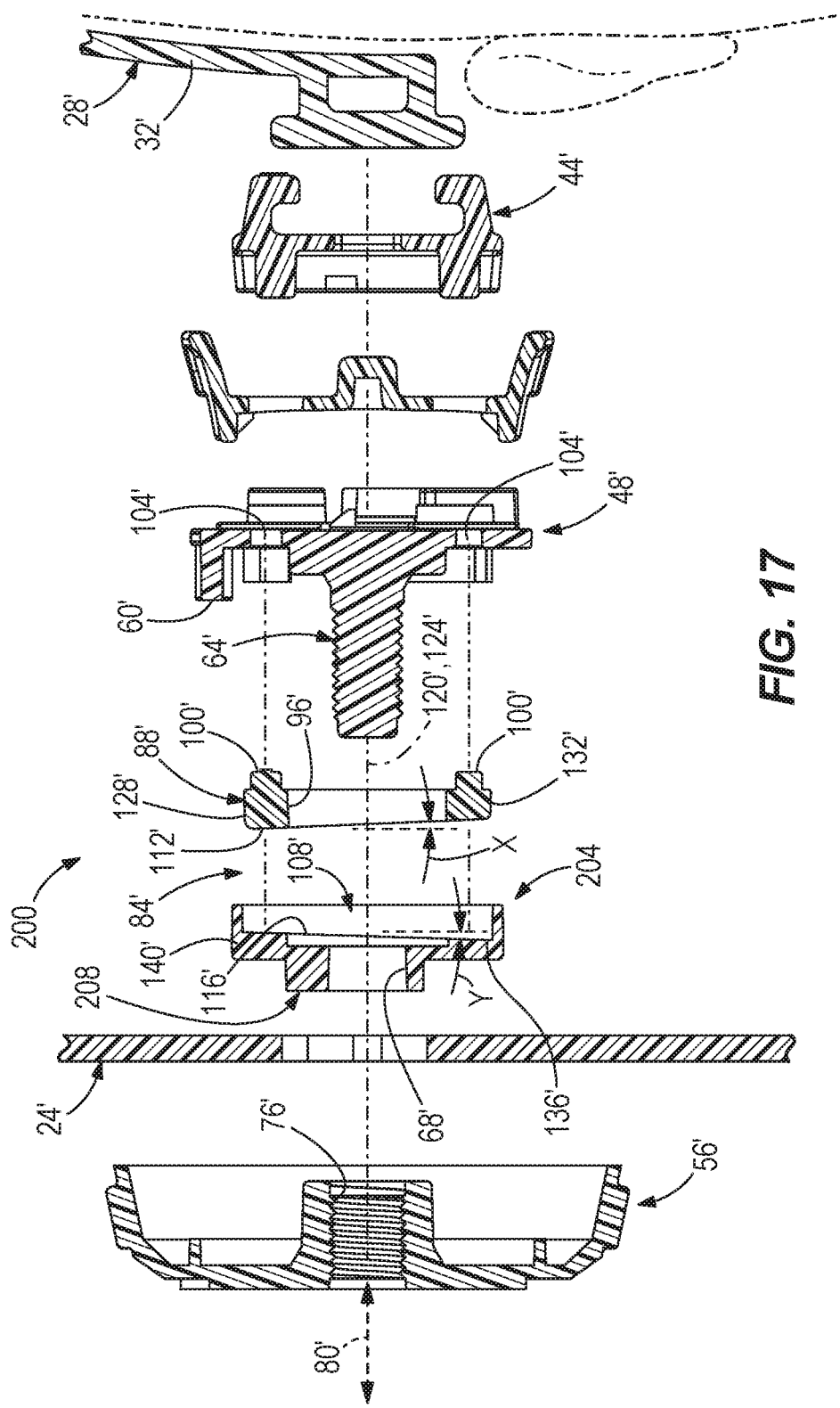

APPARATUS FOR REDUCING ANGULAR VELOCITY OF PROTECTIVE SHELLS ASSOCIATED WITH PROTECTIVE HEADWEAR

RELATED APPLICATIONS

The present application claims the priority benefit of U.S. Provisional Patent Application No. 62/096,948, filed Dec. 26, 2014, which is incorporated by reference herein in its entirety.

FIELD OF THE INVENTION

The present disclosure generally relates to protective headwear and, more particularly, to movement of protective headwear relative to a user's head.

BACKGROUND

Several types of protective headwear exist. Welding helmets are one example of protective headwear and some conventional welding helmets include an outer protective shell and headgear for supporting the outer shell on a user's head. The outer shell at least partially surrounds a user's head to provide protection.

One common activity that most welders perform on a daily basis is nodding of their welding helmets in order to move the outer shell from an upward, inoperative position, to a downward, operative position. The nodding motion, which may be comprised of a quick snap of the neck, applies stress on a user's neck muscles that can lead to long term neck issues. Additionally, the user's neck muscles can also be strained when they absorb a force generated by the outer shell coming to a jarring stop at a bottom limiting position.

Most welders do not recognize the health risk this daily action causes as the potential injury often manifests after a long period of time. Moreover, neck discomfort is accepted as the norm in the welding profession due to the rigorous requirements associated therewith. Significant angular velocity is created between the outer shell and the headgear of the protective headwear when a user nods the protective headwear.

Some conventional welding helmets allow a user to statically increase/decrease a normal force to increase/reduce the angular velocity of the outer shell relative to the headgear. Such welding helmets increase/reduce the angular velocity at a location where the outer shell pivots relative to the headgear. This is achieved in such welding helmets using a threaded fastener and a corresponding nut or knob, which can be rotated relative to the threaded fastener in either direction resulting in movement of the nut along the threaded fastener in both directions. A wall of the outer shell of the protective headwear is positioned between the nut and the headgear, and movement of the nut toward the outer shell and headgear applies more force, friction or normal force to the outer shell wall to decrease the angular velocity capable between the outer shell and the headgear. Movement of the nut away from the outer shell wall and the headgear reduces the force, friction or normal force applied to the outer shell wall to increase the angular velocity capable between the outer shell and the headgear.

One issue with tightening the nut and increasing the normal force is that, while it does reduce the angular velocity, it also increases the required applied force to overcome static friction between the pivoting components. As a result, more strain is applied on neck muscles due to a more violent nodding motion to initiate pivoting of the outer shell downward relative to the headgear.

Conversely, if the nut is too loose, then the initial nodding becomes easier, but the outer shell quickly accelerates to come to a jarring stop as it slams down on a stop member at a bottom limiting position. At the bottom limiting position, the force of impact is transmitted mostly to a user's neck muscles.

SUMMARY

Thus, a need exists for protective headwear that resolves one or more of these deficiencies. Additionally, a need exists for manners of minimizing forces exerted on a user's neck muscles from the nodding motion to help users of protective headwear avoid long term neck problems.

In one aspect, protective headwear automatically increases a normal force between an outer shell and headgear of protective headwear as the outer shell pivots relative to the headgear from an upper, inoperative position to a downward, operative position.

In one aspect, protective headwear dynamically reduces an angular velocity of an outer shell relative to headgear of protective headwear as the outer shell pivots relative to the headgear from an upper, inoperative position to a downward, operative position.

In one aspect, protective headwear provides an increasing frictional or resistive force between an outer shell and headgear of the protective headwear to reduce an angular velocity of the outer shell relative to the headgear as the outer shell pivots relative to the headgear from an upper, inoperative position to a downward, operative position.

In one aspect, a protective headwear is provided and includes headgear including at least one strap, an outer shell rotatably coupled to the headgear, and a friction member configured to reduce angular velocity of the outer shell relative to the headgear.

In one aspect, a welding helmet is provided and includes a support member configured to engage a user's head, an outer shell rotatably coupled to the support member and moveable relative to the support member between a first position and a second position, and a member coupled between the support member and the outer shell to reduce angular velocity of the outer shell as it moves between the first position and the second position. The first position may be an upward, inoperative position and the second position may be a downward, operative position.

In one aspect, a protective headwear is provided and includes a support member configured to engage a user's head, an outer shell coupled to the support member and rotatable relative to the support member between a first position and a second position, and a member coupled between the support member and the outer shell to reduce angular velocity of the outer shell as it moves from the first position to the second position.

In one aspect, the first position may be an upward, inoperative position and the second position may be a downward, operative position.

In one aspect, the member may include a first portion and a second portion formed separately from each other and may be moveable relative to each other as the outer shell moves from the first position to the second position.

In one aspect, the first portion may include a first surface and the second portion may include a second surface. The first surface and the second surface may engage each other.

In one aspect, the outer shell may rotate about an axis. The first portion may include a first surface and the second portion may include a second surface. At least one of the first surface and the second surface may be non-perpendicularly oriented relative to the axis.

In one aspect, the at least one of the first surface and the second surface may be angled between about 0.25 degrees and about 45 degrees from perpendicularity with the axis.

In one aspect, the at least one of the first surface and the second surface may be angled between about 0.5 degrees and about 2 degrees from perpendicularity with the axis.

In one aspect, both the first surface and the second surface may be non-perpendicularly oriented relative to the axis.

In one aspect, the axis may extend through the first portion and the second portion.

In one aspect, the first portion may define a first aperture therein and the second portion may define a second aperture therein. The axis may align with and may extend through the first and second apertures.

In one aspect, the member may provide a normal force to the outer shell with the outer shell moving from the first position to the second position.

In one aspect, the normal force may increase as the outer shell moves further from the first position and toward the second position.

In one aspect, the member does not reduce angular velocity of the outer shell relative to the headgear with the outer shell moving from the second position to the first position.

In one aspect, the protective headwear may further include a coupling member coupled to and rotatable with the outer shell. The coupling member may include one of the first portion and the second portion of the member.

In one aspect, the one of the first portion and the second portion of the member may be unitarily formed as one-piece with the coupling member.

In one aspect, the other one of the first portion and the second portion may be formed separately from the coupling member. The coupling member and the one of the first portion and the second portion may rotate relative to the other one of the first portion and the second portion.

In one aspect, the member may be a spring.

In one aspect, the support member may be headgear including at least one strap.

In one aspect, the protective headwear may be a welding helmet.

In one aspect, a protective headwear is provided and includes headgear including at least one strap, an outer shell coupled to the headgear and rotatable about an axis relative to the headgear between a first position and a second position, and a coupling member coupled to and rotatable with the outer shell. The coupling member includes a first surface oriented non-perpendicularly relative to the axis and the axis extends through the coupling member. The protective headwear also includes a member formed separately from the coupling member and including a second surface oriented non-perpendicularly relative to the axis. The first surface engages the second surface and is rotatable relative to the second surface, and the axis extends through the member. Engagement between the first surface and the second surface reduces angular velocity of the outer shell as the outer shell rotates from the first position to the second position.

In one aspect, engagement of the first surface and the second surface may provide a normal force to the outer shell as the outer shell rotates from the first position to the second position.

In one aspect, the normal force increases as the outer shell moves further from the first position and toward the second position.

BRIEF DESCRIPTION OF THE DRAWINGS

The disclosure can be better understood with reference to the following drawings and description. The components in the figures are not necessarily to scale, emphasis instead being placed upon illustrating principles of the disclosure.

FIG. 17 is an exploded elevational view of a portion of the protective headwear of FIG. 15, according to one aspect of the present disclosure.

DETAILED DESCRIPTION

Figure 1:
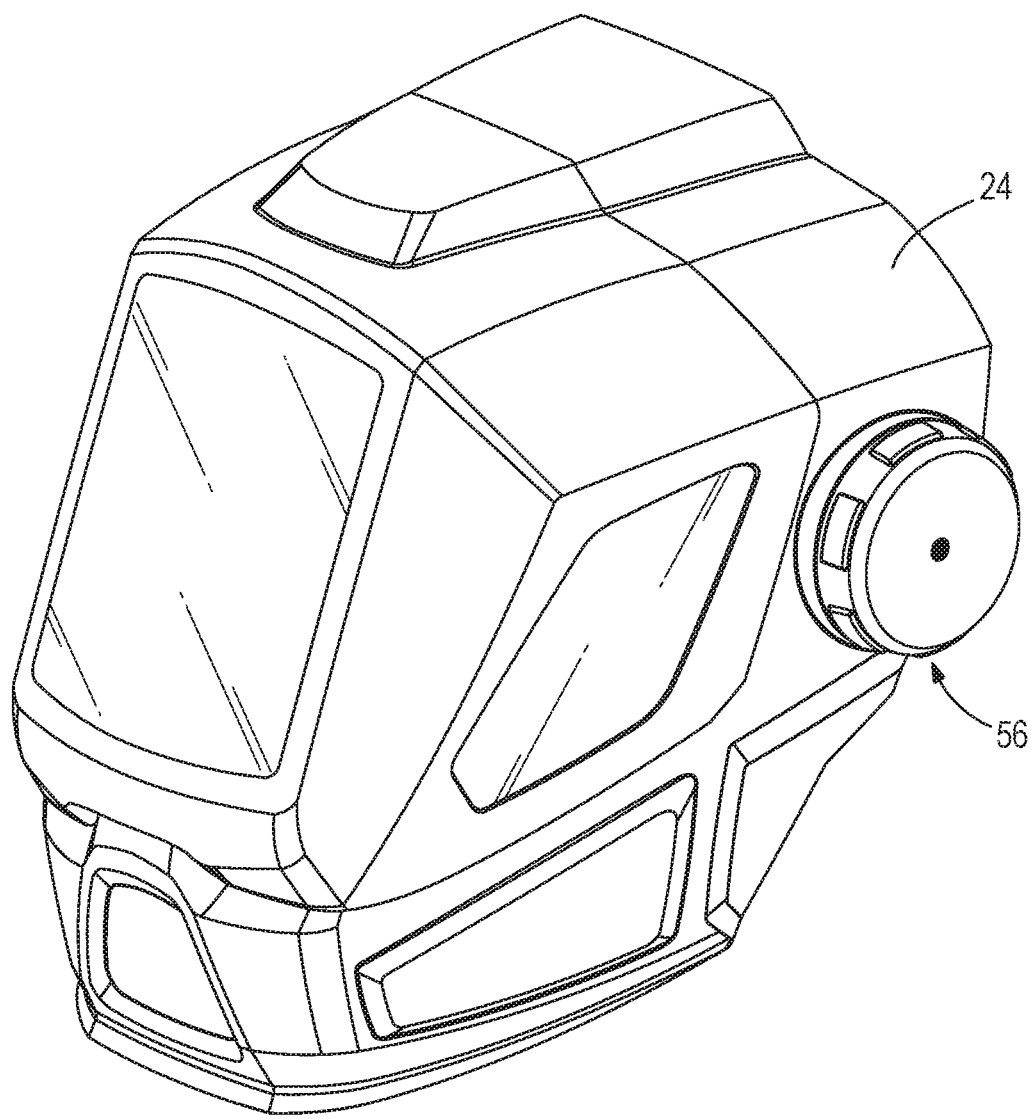
FIG. 1 is a top perspective view of one example of protective headwear, according to one aspect of the present disclosure.
Figure 3:
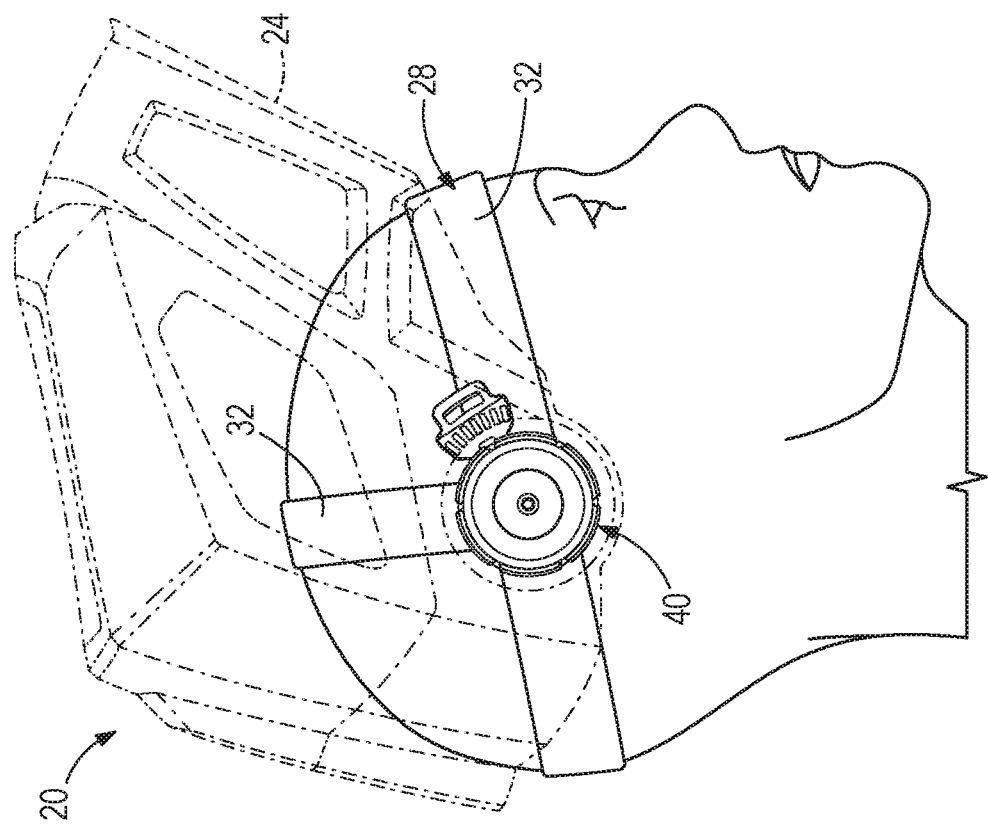
FIG. 3 is an elevational view of the protective headwear of FIG. 1 shown with the outer shell of the protective headwear in an upward or inoperative position, according to one aspect of the present disclosure.
Figure 2:
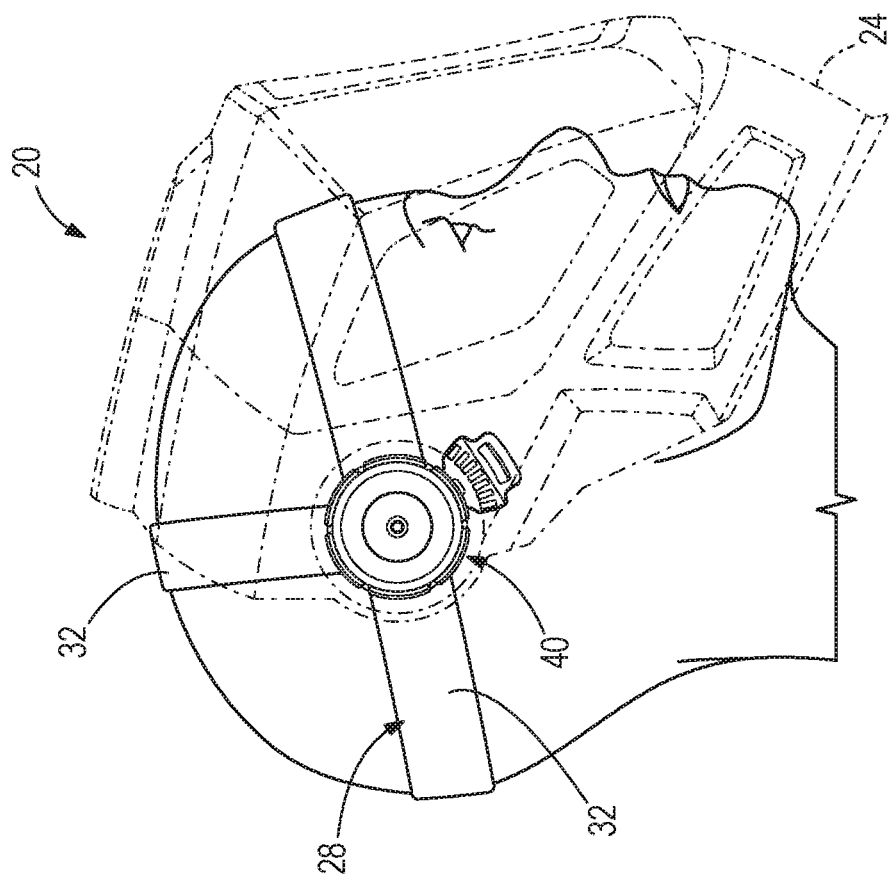
FIG. 2 is an elevational view of the protective headwear of FIG. 1 shown with an outer shell of the protective headwear in a downward or operative position, according to one aspect of the present disclosure.
Figure 4:
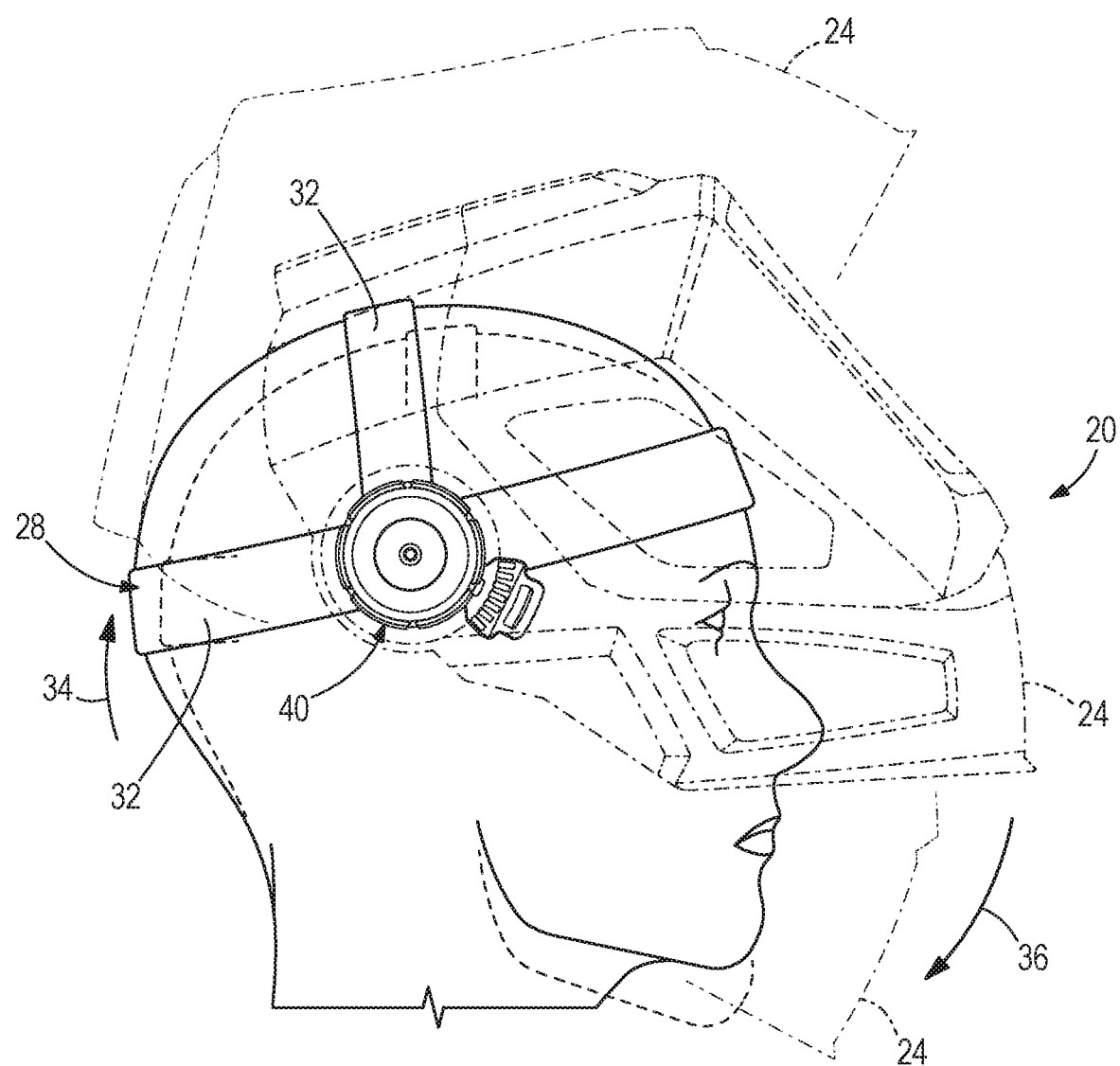
FIG. 4 is an elevational view of the protective headwear of FIG. 1 shown with the outer shell of the protective headwear in an intermediate position between the upward and downward positions initiated by a nod of a user's head, according to one aspect of the present disclosure.

Users are required to wear protective headwear 20 in a variety of environments in an attempt to provide protection to the users' heads. Protective headwear 20 generally has more weight than a typical baseball cap or other non-protective headwear 20, thereby applying stress to a user's neck. Many types of protective headwear 20 exist and include, but are not limited to, hard hats, welding helmets, grinding helmets, etc. Some of the protective headwear 20 include moveable components that can apply additional stress to a user's neck. For example, increased stress may be applied to a user's neck to initiate movement of the components, during movement of the components, and/or upon stopping of the components movement. One example of protective headwear 20 that includes moving components is a welding helmet 20. For purposes of demonstrating at least some of the principles of the present disclosure, a welding helmet 20 will be illustrated and described. However, the illustration and description of a welding helmet is not intended to limit the present disclosure in any manner. Rather, the principles of the present disclosure may apply to any type of protective headwear 20.

Referring now to FIGS. 1-8, one example of protective headwear 20 is illustrated. In this example, the protective headwear 20 is a welding helmet 20 commonly used during welding processes to protect a user's eyes, face and head from harmful conditions occurring as a result of a welding process. The welding helmet 20 includes a protective outer shell 24 and headgear or a support member 28. The headgear 28 is supported on a user's head and includes one or more straps or bands 32 that encompass, are supported on and/or engage at least a portion of a user's head to support the welding helmet 20 on the user's head. The outer shell 24 is made of a hard material such as, for example, hard plastic, and is rotatably coupled to the headgear 28. The outer shell 24 is rotatable relative to the headgear 28 between a downward or operative position (see FIG. 2), in which the outer shell 24 is positioned over a user's eyes and face to provide protection thereto, and an upward or inoperative position (see FIGS. 1 and 3), in which the outer shell 24 is positioned above and out from in front of a user's eyes and face to inhibit obstruction of the user's eyes and face (e.g., unobstructed viewing by the user, allowing fresh and/or ambient air to access the user's face, etc.).

During a welding process, a user may desire to move the outer shell 24 between the upward and downward positions. Oftentimes, a user's hands are occupied by tools and/or objects to be welded, thereby leaving no free hand(s) to rotate the outer shell 24 relative to the headgear 28. Commonly, a user will position the outer shell 24 in the upward position. When the user is ready to initiate another welding process, the user grips the welding tool with one hand, an object to be welded with the other hand, and quickly nods (nod represented, for example, by arrow 34 in FIG. 4) his/her head forward to cause the outer shell 24 to initiate rotation relative to the headgear 28 (see FIG. 4) from the upward position to the downward position. The outer shell 24 has an angular velocity (represented, for example, by arrow 36 in FIG. 4) as it moves from the upward position to the downward position as a result of the user's nod. The outer shell 24 continues to rotate until it reaches a bottom limiting position.

Figure 5:
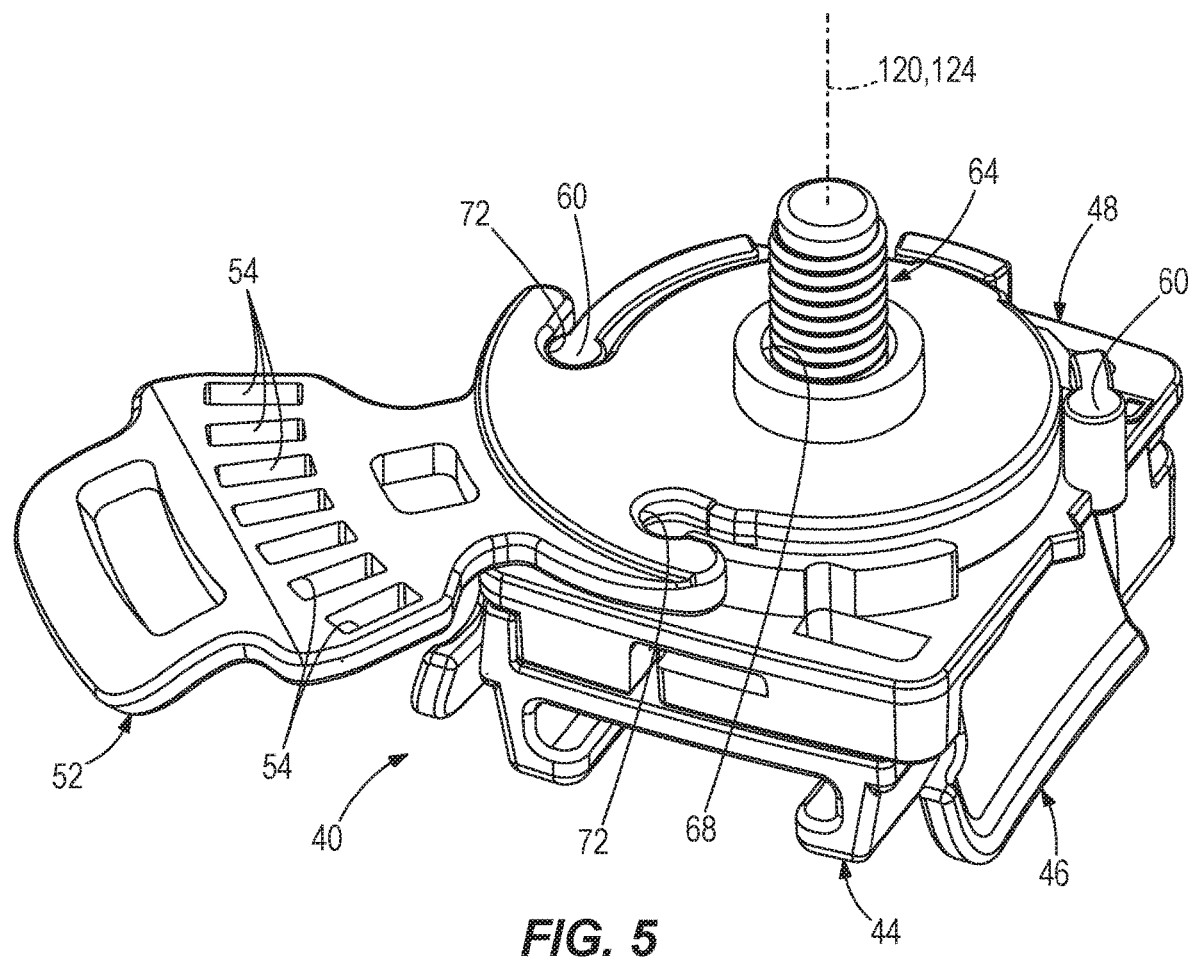
FIG. 5 is a perspective view of one example of a portion of the protective headwear of FIG. 1, according to one aspect of the present disclosure.
Figure 6:
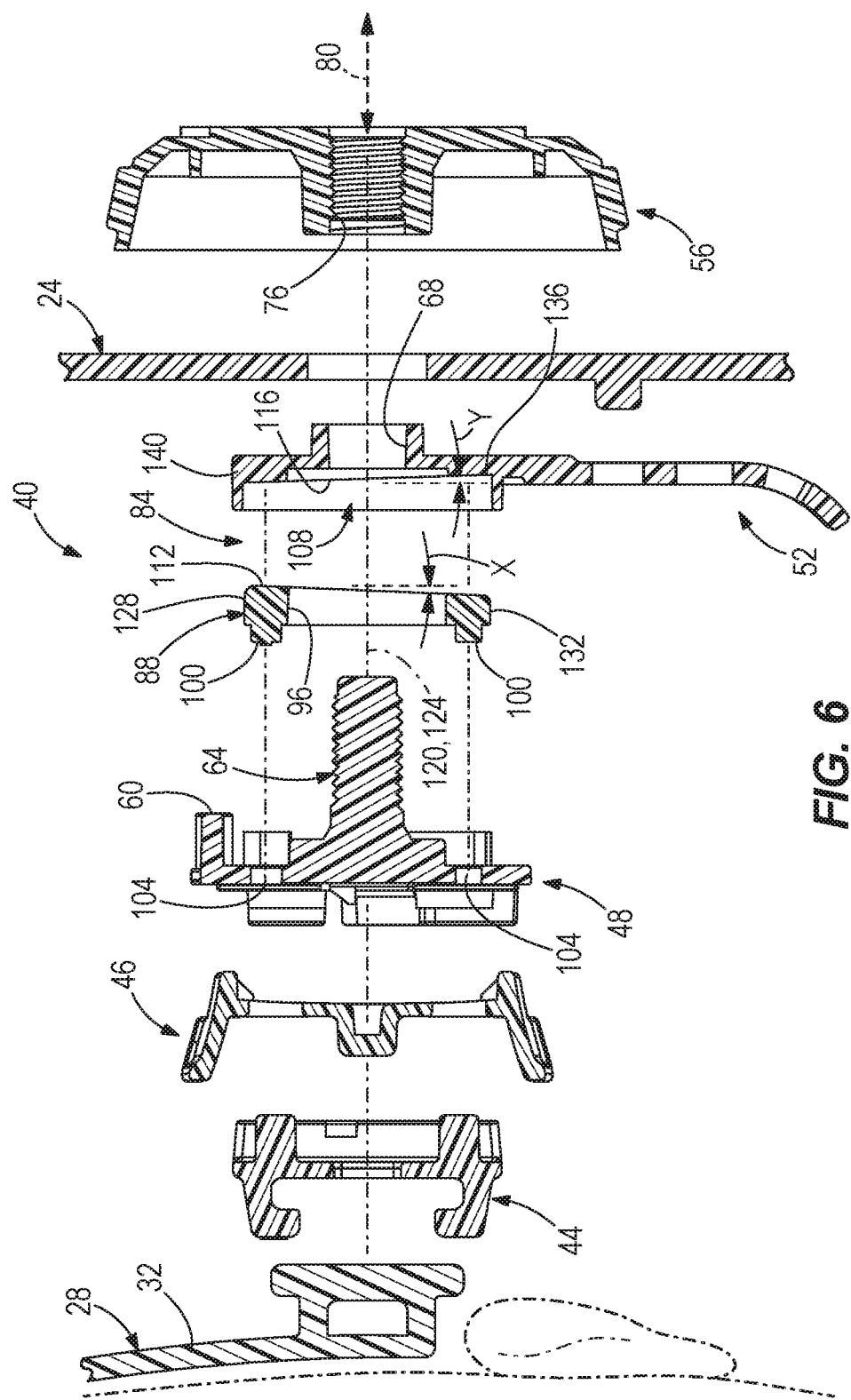
FIG. 6 is an exploded elevational view of a portion of the protective headwear of FIG. 1, according to one aspect of the present disclosure.
Figure 7:
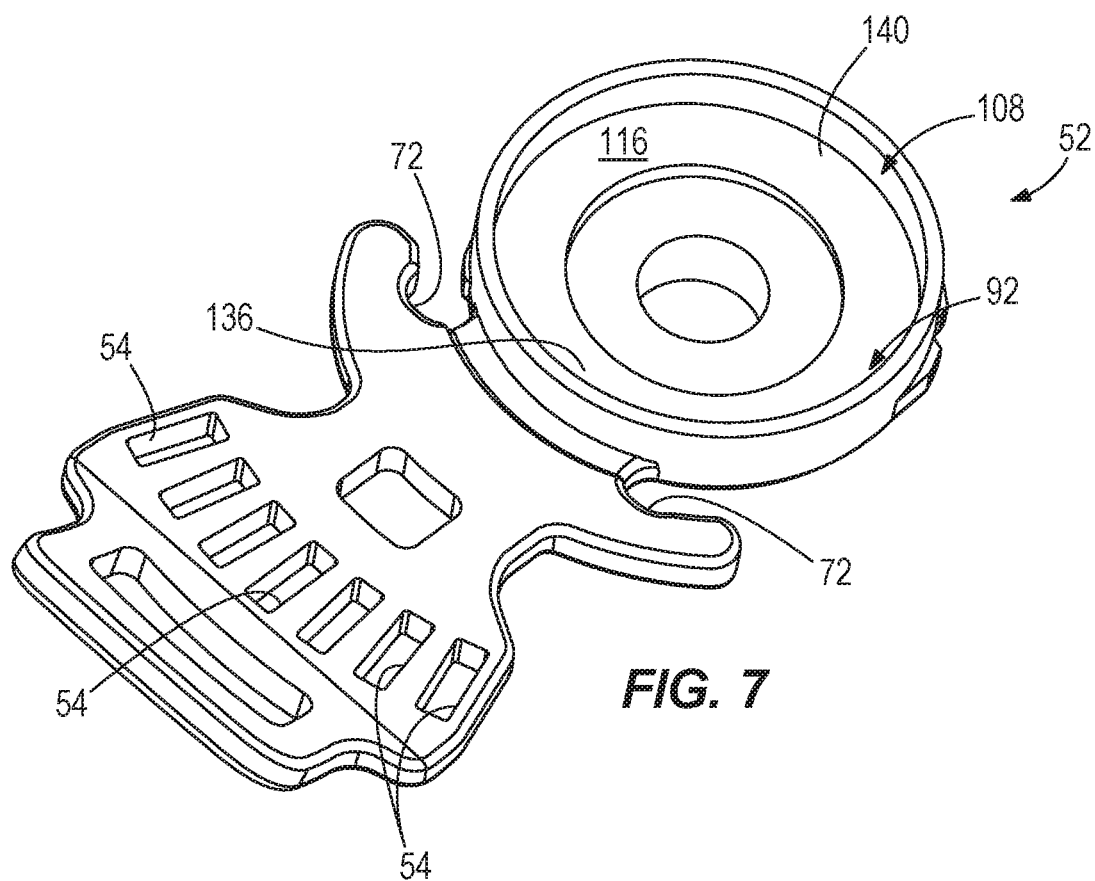
FIG. 7 is a perspective view of one example of a coupling member of the protective headwear of FIG. 1, according to one aspect of the present disclosure.
Figure 8:
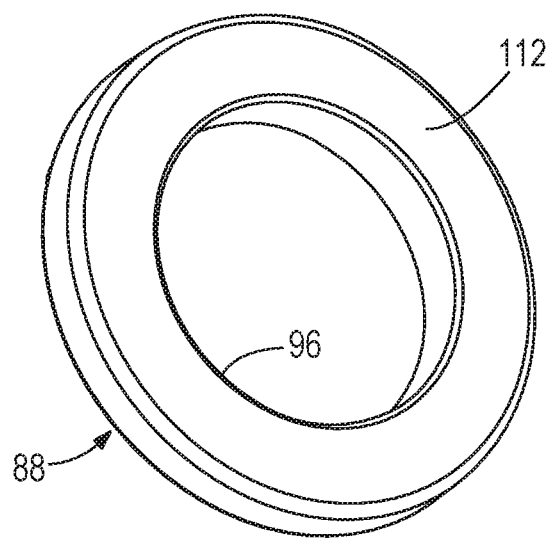
FIG. 8 is a perspective view of one example of at least a portion of a friction member of the protection headwear of FIG. 1, according to one aspect of the present disclosure.
Figure 9:
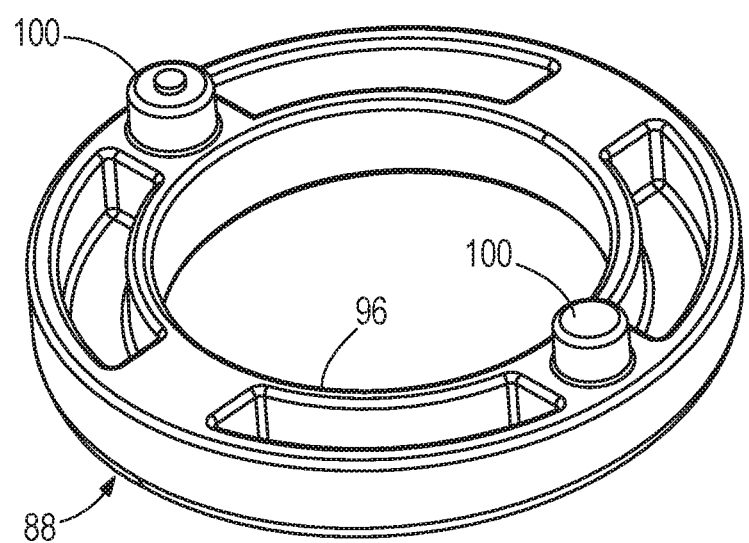
FIG. 9 is another perspective view of the at least a portion of the friction member of FIG. 8, according to one aspect of the present disclosure.
Figure 10:
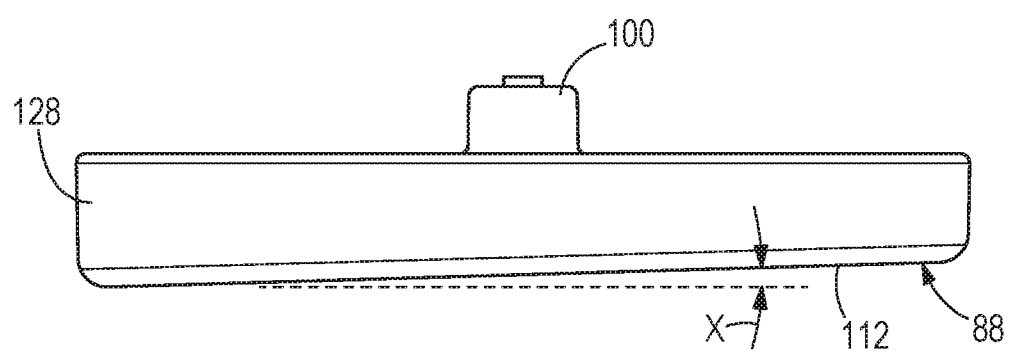
FIG. 10 is an elevational view of the at least a portion of the friction member of FIG. 8, according to one aspect of the present disclosure.

Referring now to FIGS. 5 and 6, one example of at least a portion of a rotation assembly 40 is illustrated. The rotation assembly 40 at least partially facilitates rotation of the outer shell 24 relative to the headgear 28. It should be understood that more or less components of the welding helmet 20 may be considered part of the rotation assembly 40 and the description included herein pertaining to the rotation assembly 40 is not intended to limit the present disclosure in any manner. It should also be understood that the illustrated example of the rotation assembly 40 is only one example and that the protective headwear 20 is capable of including many other types, configurations and embodiments of rotation assemblies, with all of such possibilities intended to be within the spirit and scope of the present disclosure.

In one example, a rotation assembly 40 is positioned on both sides of a protective headwear 20. In another example, a rotation assembly 40 is positioned on only one side of the protective headwear 20. In such an example where a rotation assembly 40 is positioned on one side of a protective headwear, the other or opposite side of the protective headwear may include a portion of the components of the rotation assembly 40, a threaded fastener and nut or knob combination, a conventional manner of facilitating rotation of the outer shell relative to the headgear, or any other manner of facilitating rotation of the outer shell relative to the headgear on the other or opposite side of the protective headwear.

In the illustrated example, the rotation assembly 40 includes a slider 44, an actuator 46, a base 48, a coupling member 52 and a knob or actuator 56. The slider 44 is coupled to the headgear 28 and is configured to move or slide along the headgear 28 to adjust a position of the rotation assembly 40 (and therefore the outer shell 24) relative to the headgear 28. The actuator 46 is coupled to the slider and the headgear 28 and is configured to selectively secure and unsecure the slider 44 relative to the headgear 28. In one example, the actuator 46 may be actuated or manipulated by a user to unsecure the slider 44 from the headgear 28 to allow the slider to move along the headgear 28. The actuator 46 may then be released by a user to cause the slider 44 to secure to the headgear and inhibit movement of the slider 44 relative to the headgear 28. The base 48 is rigidly coupled to the slider 44 and is moveable with the slider 44 relative to the headgear 28. The base 48 includes a pair of stops or projections 60 respectively engageable by the coupling member 52 in the upward and downward positions. The base 48 also includes a threaded member, projection or post 64 extending outward away from the headgear 28. The coupling member 52 is rigidly coupled to the outer shell 24 to ensure the coupling member 52 is rotatable with the outer shell 24 relative to the headgear 28. In the illustrated example, the coupling member 52 includes a plurality of connectors 54 to provide a variety locations where the outer shell 24 may connect to the coupling member 52. This variability in positioning allows a user to position the outer shell 24 relative to the user's face in a variety of orientations. The coupling member 52 is rotatably coupled to the base 48 and defines an aperture 68 therein configured to allow the threaded member 64 to pass there through. The outer shell 24 is rigidly coupled to the coupling member 52 and is rotatable with the coupling member 52 relative to the headgear 28 and base 48. The coupling member 52 defines a pair of slots 72 therein. Rotation of the coupling member 52 is limited in one direction when one of the stops 60 engages an end of one of the slots 72 and limited in the other direction when the other of the stops 60 engages an end of the other slot 72. The outer shell 24 is positioned in the upward position when one of the stops 60 engages the end of one of the slots 72 and is in the downward position when the other stop 60 engages the end of the other slot 72. The actuator 56 defines a cavity 76 including threads complementary to the external threads on the threaded member 64. The actuator 56 is rotatable in both directions (e.g., clockwise and counter-clockwise) relative to the threaded member 64, which results in movement of the actuator 56 along the threaded member 64 in either direction. By rotating the actuator 56 in a first direction and threading the actuator 56 toward the outer shell 24 and headgear 28, a normal force (represented, for example, by arrow 80 in FIG. 6) applied to the outer shell 24 increases. Conversely, by rotating the actuator 56 in a second direction and threading the actuator 56 away from the outer shell 24 and the headgear 28, the normal force applied to the outer shell 24 decreases. A user may position the actuator 56 along the threaded member 64 as desired to apply a desired amount of normal force to the outer shell 24.

The rotation assembly 40 is configured to reduce angular velocity of the outer shell 24 relative to the headgear 28 as the outer shell 24 moves from the upward position to the downward position. The rotation assembly 40 is capable of achieving this reduction in angular velocity in a variety of manners and is capable of having a variety of different configurations in order to achieve this reduction in angular velocity. In one example, the rotation assembly 40 may include a resistance or friction member 84 that reduces the angular velocity of the outer shell 24 relative to the headgear 28 as the outer shell 24 moves from the upward position to the downward position. In some examples, the friction member 84 may increasingly reduce the angular velocity of the outer shell 24 the further along or closer the outer shell 24 gets to the bottom limiting position. The friction member 84 may have a variety of configurations in order to achieve this reduction in angular velocity.

One example of a friction member 84 is illustrated in FIGS. 6-10. In this example, the friction member 84 includes a first portion 88 and a second portion 92. In the illustrated example, the first portion 88 is formed separately from and is coupled to the base 48 and the second portion 92 is unitarily formed as one-piece with the coupling member 52. In one example, the first portion 88 may be unitarily formed as one-piece with the base 48. In one example, the second portion 92 may be formed separately from and coupled to the coupling member 52. In one example, both the first portion 88 and the second portion 92 are respectively unitarily formed as one-piece with the base 48 and the coupling member 52. In one example, both the first portion 88 and the second portion 92 are formed separately from the respective base 48 and the coupling member 52.

In the illustrated example, the first portion 88 is generally circular in shape (or disk shaped) and defines an aperture 96 there through. In other examples, the first portion 88 may have other shapes and all of such possibilities are intended to be within the spirit and scope of the present disclosure. In one example, the first portion 88 includes a pair of projections 100 positioned in complementary shaped apertures 104 defined in the base 48 to inhibit the first portion 88 from rotating relative to the base 48. The second portion 92 is formed within a cavity 108 of the coupling member 52. In the illustrated example, the second portion 92 has a complementary shape (i.e., circular or disk shaped) to the first portion 88. Accordingly, since the first portion 88 may have a wide variety of shapes, the second complementary portion may also have a wide variety of shapes.

In the illustrated example, the first portion 88 includes a surface 112 and the second portion 92 includes a surface 116. The two surfaces 112, 116 are configured to engage each other. As the coupling member 52 rotates relative to the first portion 88, the surface 116 of the coupling member 52 engages the surface 112 of the first portion 88 to provide a friction force or resistance force counter to an angular velocity of the outer shell 24 and coupling member 52 as they move from the upward position to the downward position. The friction force or resistive force may also be referred to as a normal force. This force created by the friction member 84 reduces the angular velocity of the outer shell 24 as it moves from the upward position to the downward position. In the illustrated example, the two surfaces 112, 116 are substantially planar.

In one example, the two surfaces 112, 116 of the friction member 84 may be substantially perpendicular to a longitudinal axis 120 of the threaded member 64 or a pivot axis 124 of the outer shell 24. In the illustrated example, the two axes 120, 124 are co-linear (and, accordingly, parallel). In other examples, the two axes 120, 124 may be offset from each other and/or non-parallel.

In one example, one of the two surfaces 112, 116 may be substantially perpendicular to at least one of the axes 120, 124 and the other of the two surfaces 112, 116 may be angled and non-perpendicular relative to at least one of the axes 120, 124.

In one example, the two surfaces 112, 116 of the friction member 84 may be angled and non-perpendicular relative to at least one of the axes 120, 124. With particular reference to FIGS. 6-10, one example of the two surfaces 112, 116 of the friction member 84 being angled and non-perpendicular to at least one of the axes 120, 124 is illustrated. The surface 112 of the first portion 88 may be at an angle X from perpendicularity of at least one of the axes 120, 124 and the surface 116 of the second portion 92 may be at an angle Y from perpendicularity of at least one of the axes 120, 124. In some examples, angle X and angle Y may be the same angle. In other examples, the angle X and angle Y may be about the same angle. In other examples, angle X and angle Y may be different angles. In one example, angle X and angle Y may be between about 0 degrees and about 90 degrees. In one example, angle X and angle Y may be between about 0.25 degrees and about 45 degrees. In one example, angle X and angle Y may be between about 0.5 degrees and about 10 degrees. In one example, angle X and angle Y may be between about 0.5 degrees and about 2 degrees.

Figure 11:
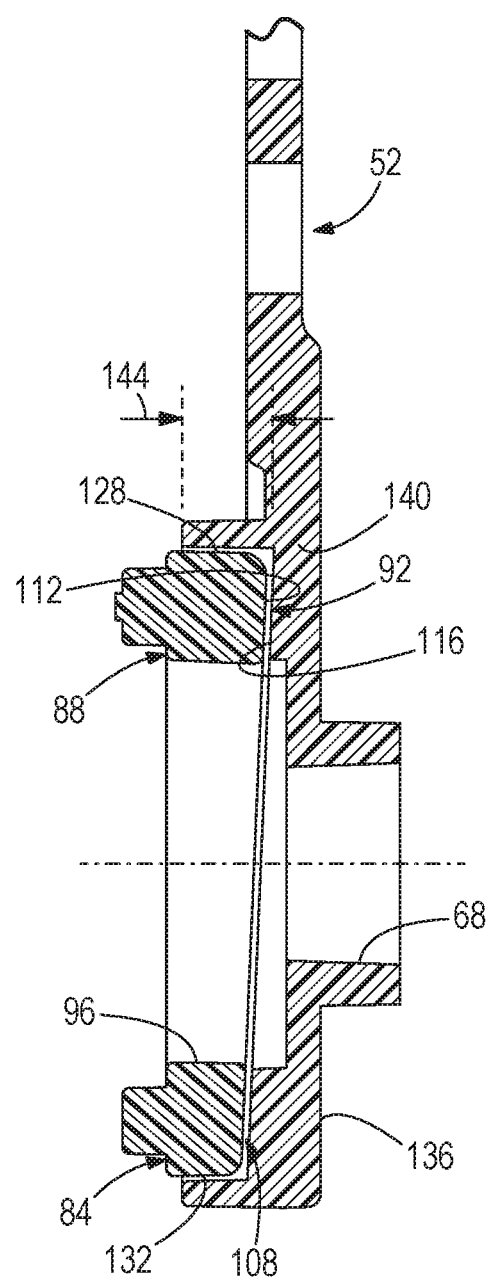
FIG. 11 is an elevational view of a portion of the protective headwear of FIG. 1 shown in the upward or inoperative position, according to one aspect of the present disclosure.
Figure 12:
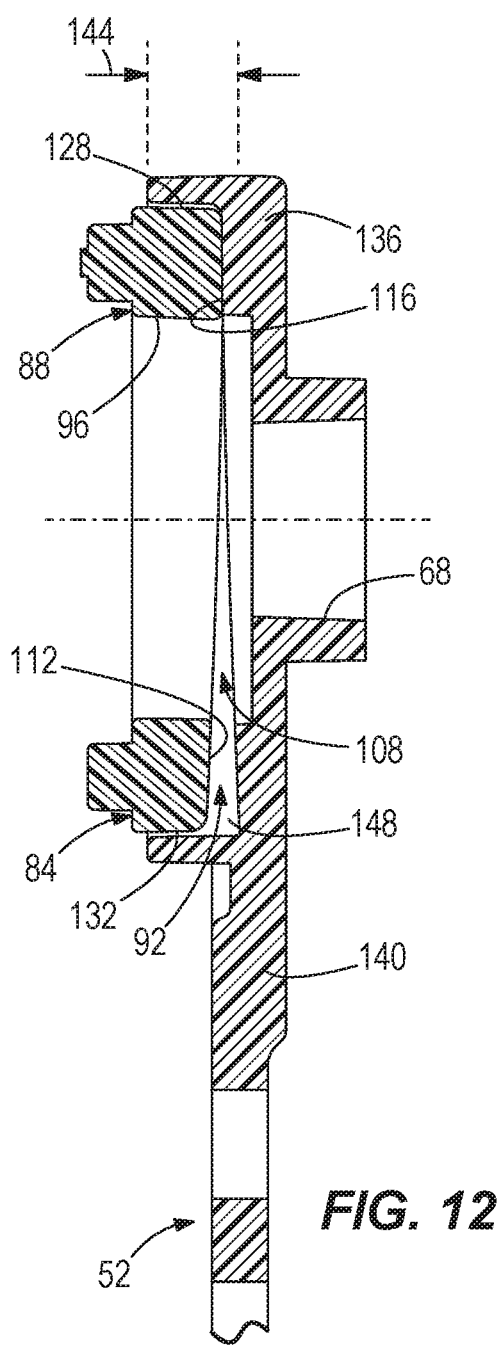
FIG. 12 is an elevational view of the portion of the protective headwear of FIG. 11 shown in the downward or operative position, according to one aspect of the present disclosure.

Referring now to FIGS. 11 and 12, operation of the friction member 84 will be described in more detail as the outer shell 24 moves from the upward position to the downward position. For simplicity, FIG. 11 illustrates the first portion 88 and the second portion 92 of the friction member 84 along with the coupling member 52 as they are oriented with the outer shell 24 in the upward, inoperative position. As illustrated, the two surfaces 112, 116 are generally parallel to each other and may engage or be spaced-apart from one another. The first portion 88 is thicker 128 at a first end (top as illustrated in FIG. 11) and thinner 132 at a second end (bottom as illustrated in FIG. 11), thereby providing the angled surface 112. The surface 116 of the second portion 92 is angled complementary and generally parallel to the surface 112 of the first portion 88 in this position by having oppositely positioned thicker portion 136 or a first end (bottom end as illustrated in FIG. 11) and thinner portion 140 or a second end (top end as illustrated in FIG. 11).

When a user nods his/her head, the outer shell 24 and the coupling member 52 begin to rotate relative to the first portion 88 of the friction member 84. As the coupling member 52 and second portion 92 rotate relative to the first portion 88, the surface 116 of the second portion 92 engages the surface 112 of the first portion 88. The surfaces 112, 116 are no longer complementarily orientated. The thicker portions 128, 136 of the first portion 88 and the second portion 92 begin to engage each other and compress together since a lateral distance 144 occupied by the first and second portions 88, 92 does not increase. This engagement increases a resistance force between the coupling member 52 and the first portion 88 of the friction member 84. This resistance force continues to increase until the coupling member 52 and the outer shell 24 are positioned in the downward, operative position as illustrated in FIG. 12. The increase in resistance force acts against the angular velocity of the outer shell 24 to slow movement of the outer shell 24 toward the downward, operative position. The angular velocity of the outer shell 24 may want to increase the further along its downward path the outer shell 24 travels, but the increase in resistance force caused by the friction member 84 offsets, at least in part, the increase in angular velocity to maintain a slowly descending outer shell 24. As shown in FIG. 12, it is possible that a gap 148 is provided between thinner portions 132, 140 of the first portion 88 and the second portion 92.

The resistance force provided by this configuration of the friction member 84 may be considered a normal force and may resist or act against the angular velocity of the outer shell 24, thereby decreasing an amount of force transferred to a user's neck when the outer shell 24 and coupling member 52 come to a stop at the bottom, operative position. The outer shell 24 and coupling member 52 slowly come to a rest at the bottom, operative position with the illustrated welding helmet 20 rather than crashing down at a high rate at the bottom, operative position for a conventional welding helmet.

In one example, the first portion 88 and the second portion 92 are made of the same material. In one example, the first portion 88 and the second portion 92 are made of different materials. In one example, the first portion 88 is made of a single material and the second portion 92 is made of a single material. In one example, the first portion 88 is made of multiple materials and the second portion 92 is made of multiple materials. In one example, one of the first portion 88 and the second portion 92 is made of a single material and the other of the first portion 88 and the second portion 92 are made of multiple materials. In examples where one or more of the first portion 88 and the second portion 92 is/are made of multiple materials, the first portion 88 and/or the second portion 92 may be made of a first material and the surface(s) 112, 116 of the first portion 88 and/or the second portion 92 may be coated or overmolded with a second material. In one example, the entire surface(s) 112, 116 of the first portion 88 and/or the second portion 92 may be coated or overmolded with a second material. In one example, a portion of the surface(s) 112, 116 of the first portion 88 and/or the second portion 92 may be coated or overmolded with a second material.

The first and second portions 88, 92 may be made of a wide variety of materials in any combination, and all of such possibilities are intended to be with in the spirit and scope of the present disclosure. Some examples of materials include, but are not limited to, metal, steel, plastic, rubber, polymers, etc. Different materials have different coefficients of friction. By altering the materials of the friction member 84 in any of the manners described above and other manners, the friction member 84 can perform in different manners, thereby providing a wide variety of capabilities. It should be understood that the friction member 84 may be made from a wide variety of materials and all such possibilities are intended to be within the spirit and scope of the present disclosure.

In another example, the friction member 84 may have a different configuration. In this example, the first portion is unitarily formed as one-piece with the base 48 and the surface 112 of the first portion is formed on the base 48. That is, the friction member 84 may not include a separately formed first portion and a second portion. Rather, the friction member 84 includes a first surface 112 on the base 48 and a second surface 116 on the coupling member 52. This example of the friction member 84 is capable of incorporating all of the alternatives and example described above with respect to FIGS. 6-12.

In a further example, the friction member 84 may include a first portion 88 as illustrated in FIGS. 6-12 and a second portion 92 that is formed separately from the coupling member 52. The second portion 92 may be received within the cavity 108 of the coupling member 52 and include a surface 116 similar to that illustrated in FIGS. 6-12. In this example, the second portion 92 is rigidly coupled to the coupling member 52 to ensure the second portion 92 and the coupling member 52 rotate together. In one example, the second portion 92 may be coupled to the coupling member 52 in a similar manner to how the first portion 88 is coupled to the base 48.

In other examples, the friction member 84 may include engaging surfaces 112, 116 that have different shapes and configurations. For example, the surfaces 112, 116 may be non-planar, bumpy, wavy, saw-toothed, or any of a wide variety of other shapes and configurations.

In examples where at least a portion of the friction member including an engagement surface (e.g., surfaces 112 or 116) is formed separately from another component of the rotation assembly 40, such a separately formed portion may be replaced with a new portion due to wear, damage, etc., to the portion. In examples, where the surfaces 112 or 116 are formed on a component of the rotation assembly 40 (e.g., base 48, coupling member 52, etc.), the component of the rotation assembly may be replaced with a new component due to wear, damage, etc., to the component.

Figure 13:
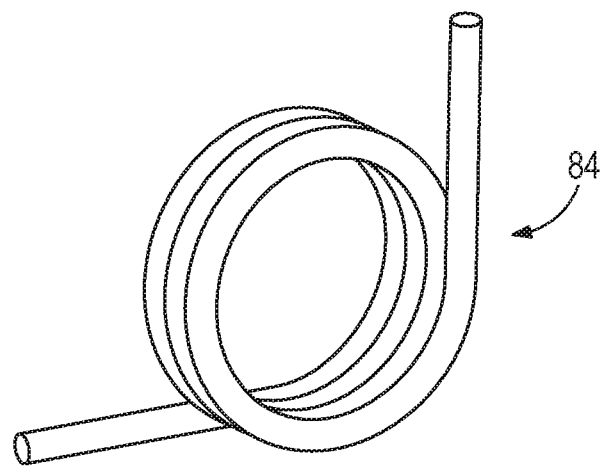
FIG. 13 is an elevational view of another example of a portion of the protective headwear of FIG. 1 shown in an upward or inoperative position, according to one aspect of the present disclosure.
Figure 14:
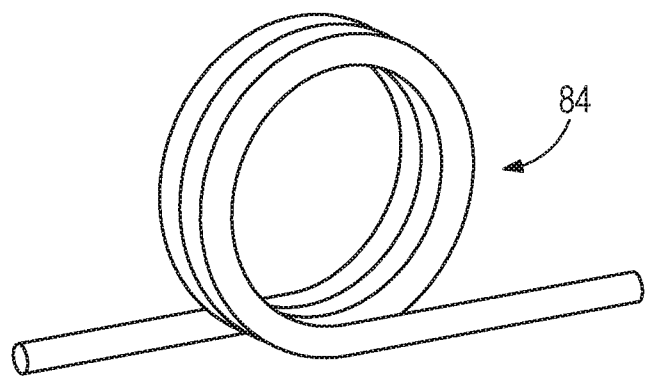
FIG. 14 is an elevational view of the portion of the protective headwear of FIG. 13 shown in a downward or operative position, according to one aspect of the present disclosure.

Referring now to FIGS. 13 and 14, another example of a friction member 84 is illustrated. In this example, the friction member 84 is a biasing member 84 such as, for example, a coil spring. The biasing member 84 may be other types of biasing members and springs and all of such possibilities are intended to be within the spirit and scope of the present disclosure. The biasing member 84 is disposed between the outer shell 24 and the headgear 28 to resist or act against the angular velocity of the outer shell 24 as it moves from the upward, inoperative position to the downward, operative position. The biasing member 84 may be positioned between the outer shell 24 and the headgear 28 in a variety of manners and all of such possibilities are intended to be within the spirit and scope of the present disclosure. For example, the biasing member 84 may be mounted between and/or engage the base 48 and the coupling member 52 to resist movement (e.g., decrease angular velocity) of the coupling member 52 relative to the base 48 from the upward position to the downward position. In another example, the biasing member 84 may be mounted between and/or engage the coupling member 52 and the headgear 28. In another example, the biasing member 84 may be mounted between and/or engage the outer shell 24 and the base 48.

Referring now to FIG. 13, the biasing member 84 is illustrated in one example of a position that corresponds to the outer shell 24 being in the upward, inoperative position. When a user nods his/her head, the outer shell 24 begins to rotate relative to the headgear 28 and the biasing member 84 begins to act against the movement of the outer shell 24 to resist movement and decrease the angular velocity of the outer shell 24. FIG. 14 illustrates the biasing member 84 in one example of a position when the outer shell 24 occupies the downward, operative position. The resistance provided by the biasing member 84 increases as the outer shell 24 moves toward the downward, operative position. The outer shell 24 and coupling member 52 slowly come to a rest at the bottom, operative position with this example of the welding helmet 20 and friction member 84 rather than crashing down at a high rate at the bottom, operative position for a conventional welding helmet. Thus, the biasing member 84 decreases the amount of force applied to the user's neck when the outer shell 24 comes to a rest at the bottom, operative position. It should be understood that the biasing member 84 may have different configurations. For example, the biasing member may be configured to occupy the position illustrated in FIG. 13 when the outer shell 24 is in the downward, operative position and occupy the position illustrated in FIG. 14 when the outer shell 24 is in the upward, inoperative position.

In other examples, the friction member 84 may include one or more hydraulic members, one or more pneumatic members, one or more geared members, one or more threaded members, a wide variety of other mechanisms, and any combination of these or other possibilities, all of which are intended to be within the spirit and scope of the present disclosure.

In still another example, the friction member 84 may include threaded members on each side of the protective headwear 20 having reverse threads relative to each other. That is, one threaded member on one side of the protective headwear 20 will have threads in a first direction and the other threaded member on the other side of the protective headwear 20 will have threads in a second direction different than the first direction. The threads on both threaded members are configured to tighten the outer shell 24 on the threaded members as the outer shell 24 rotates from the upward, inoperative position to the downward, operative position. This tightening creates an increased friction that acts against movement and decreases the angular velocity of the outer shell 24 as it rotates downward, thereby reducing the force exerted to a user's neck when the outer shell 24 comes to a stop at the bottom, operative position. Conversely, the outer shell 24 loosens on the threaded members when the outer shell 24 rotates from the downward, operative position to the upward, inoperative position. Typical protective headwear that may include threaded members on each side of the headwear have threaded members including threads in the same, single direction. Thus, as the outer shell rotates downward from the upward, inoperative position to the downward, operative position, the outer shell tightens on the threaded member on one side of the protective headwear and loosens on the threaded member on the other side of the protective headwear. The forces created by the tightening and loosing offset each other and no net gain or loss of forces is created to act against the angular velocity of the outer shell as it rotates downward.

Figure 15:
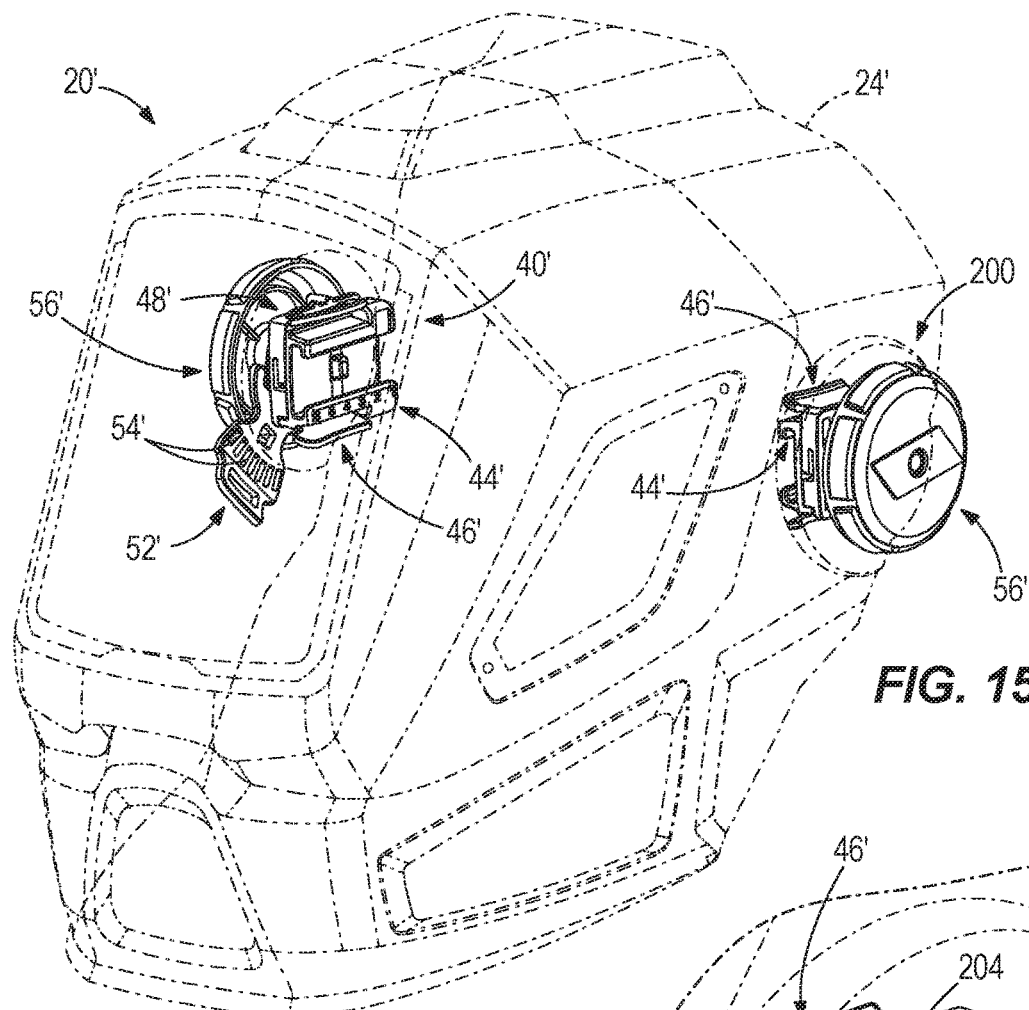
FIG. 15 is a top perspective view of another example of protective headwear, according to one aspect of the present disclosure.
Figure 16:
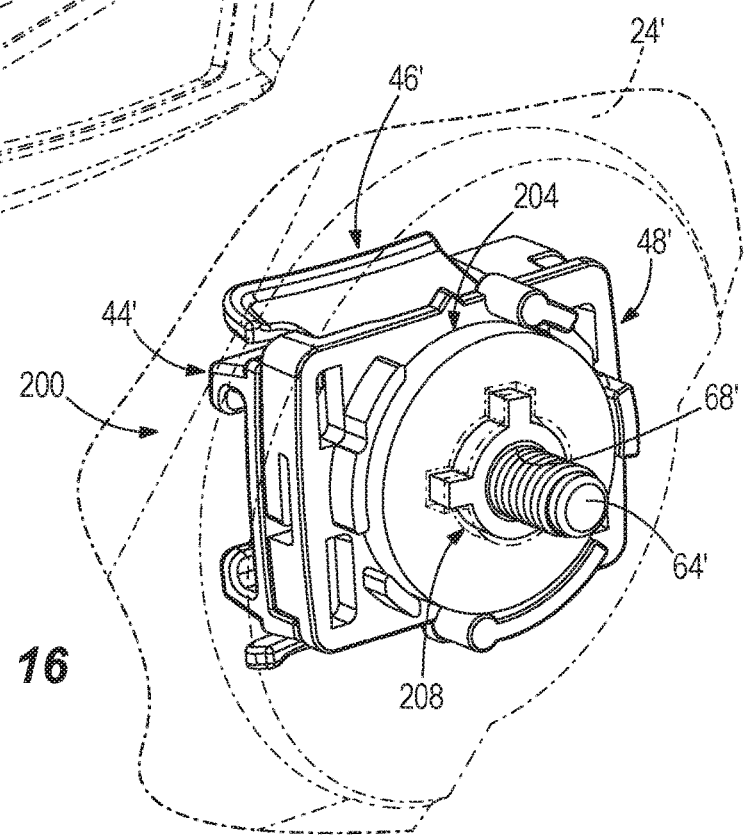
FIG. 16 is a perspective view of one example of a portion of the protective headwear of FIG. 15, according to one aspect of the present disclosure.

Referring now to FIGS. 15-17, another example of protective headwear 20' is illustrated. In this example, the protective headwear 20' includes a rotation assembly on both sides. In the illustrated example, the protective headwear 20' includes a first rotation assembly 40' on one side similar to the rotation assembly 40 illustrated in FIGS. 1-14 and a second rotation assembly 200 on an opposite side different than the first rotation assembly 40'. Since the first rotation assembly 40' in this example is similar to the rotation assembly 40 illustrated in FIGS. 1-14, the first rotation assembly 40' will not be described in detail herein. Rather, reference is made to the description above associated with FIGS. 1-14 for an understanding of the first rotation assembly 40' included in the example of the protective headwear 20' illustrated in FIGS. 15-17 of the present disclosure.

With respect to the second rotation assembly 200, the second rotation assembly 200 includes many similarities to the first rotation assembly 40'. For example, the second rotation assembly 200 includes a slider 44', an actuator 46', a base 48' and a knob or actuator 56' having similar structure and function to the slider 44, actuator 46, base 48 and knob or actuator 56 associated with the rotation assembly 40 illustrated in FIGS. 1-14. In the illustrated example, the second rotation assembly 200 includes a coupling member 204 having a different configuration than the coupling member 52' associated with the first rotation assembly 40'. In the illustrated example, the coupling member 204 does not include a plurality of connectors (like the connectors 54' included on the coupling member 52' of the first rotation assembly 40'). Instead, the coupling member 204 is connected to the outer shell 24' in a single orientation using a connector 208. The connector 208 may have any shape and configuration and be connected to the outer shell 24' in any manner and all of such possibilities are intended to be within the spirit and scope of the present disclosure.

With reference to FIGS. 16 and 17, the coupling member 204 is rotatably coupled to the base 48' and defines an aperture 68' therein configured to allow the threaded member 64' to pass there through. The outer shell 24' is rigidly coupled to the coupling member 204 and is rotatable with the coupling member 204 relative to the headgear 28' and base 48'. The remainder of the coupling member 204 includes similar structure and functionality to the coupling member 52' of the first rotation assembly 40' and reference is made to the description above associated with the coupling member 52 illustrated in FIGS. 1-14 for an understanding of this structure and functionality of the coupling member 204. For example, the second coupling member 204 includes a similar angled surface 116' to that of the coupling member 52 associated with FIGS. 1-14 and this angled surface 116' of the coupling member 204 functions similarly to the angled surface 116 of the coupling member 52.

It should be understood that all the alternatives and examples described above with respect to the rotation assembly 40 associated with FIGS. 1-14 also apply to the first and second rotation assemblies 40' and 204 associated with FIGS. 15-17.

It should also be understood that all the alternatives and examples described above with respect to the protective headwear 20 associated with FIGS. 1-14 also apply to the protective headwear 20' associated with FIGS. 15-17.

It should further be understood that the features of the present disclosure may be incorporated into different types of protective headwear. The combination of the features of the present disclosure and any type of protective headwear are intended to be within the spirit and scope of the present disclosure.

It should also be understood that use of the word "headwear" may be either singular or plural to respectively represent either a single headwear item or multiple headwear items. Unless otherwise stated, use of the word "headwear" in the claims represents a single headwear item.

It should further be understood that the use of any orientation or directional terms herein such as, for example, "top", "bottom", "front", "rear", "back", "left", "right", "side", etc., is not intended to imply only a single orientation of the item with which it is associated or to limit the present disclosure in any manner. The use of such orientation or directional terms is intended to assist with the understanding of principles disclosed herein and to correspond to the exemplary orientation illustrated in the drawings. For example, the protective headwear may be utilized in any orientation and use of such terms is intended to correspond to the exemplary orientation of the protective headwear illustrated in the drawings. The use of these terms in association with the protective headwear is not intended to limit the protective headwear to a single orientation or to limit the protective headwear in any manner.

While various embodiments of the disclosure have been described, it will be apparent to those of ordinary skill in the art that other embodiments and implementations are possible within the scope of the disclosure. Accordingly, the disclosure is not to be restricted except in light of the attached claims and their equivalents.

The invention claimed is:

1. A protective headwear comprising:
   a support member configured to engage a user's head;
   an actuator;
   an outer shell coupled to the support member and rotatable relative to the support member between a first position and a second position, the actuator moveable relative to the outer shell to apply varying levels of force to the outer shell; and
   a member coupled between the support member and the outer shell to reduce angular velocity of the outer shell as it moves from the first position to the second position;
   wherein the member includes a first portion and a second portion formed separately from each other and formed separately from the support member and the outer shell, and wherein the first portion and the second portion are moveable relative to each other as the outer shell moves from the first position to the second position;
   wherein the first portion includes a first surface and the second portion includes a second surface, wherein the first surface and the second surface directly engage each other, the first portion comprising a first bore which is asymmetrical and the second portion comprising a second bore which is asymmetrical, the outer shell disposed between the actuator and the member.

2. The protective headwear of claim 1, wherein the first position is an upward, inoperative position and the second position is a downward, operative position.

3. The protective headwear of claim 1, wherein the outer shell rotates about an axis, wherein at least one of the first surface and the second surface is non-perpendicularly oriented relative to the axis.

4. The protective headwear of claim 3, wherein the at least one of the first surface and the second surface is angled between about 0.25 degrees and about 45 degrees from being perpendicular with the axis.

5. The protective headwear of claim 4, wherein the at least one of the first surface and the second surface is angled between about 0.5 degrees and about 2 degrees from being perpendicular with the axis.

6. The protective headwear of claim 3, wherein both the first surface and the second surface are non-perpendicularly oriented relative to the axis.

7. The protective headwear of claim 3, wherein the axis extends through the first portion and the second portion.

8. The protective headwear of claim 7, wherein the first portion defines a first aperture therein and the second portion defines a second aperture therein, wherein the axis aligns with and extends through the first and second apertures.

9. The protective headwear of claim 1, wherein the member provides a second force to the outer shell with the outer shell moving from the first position to the second position.

10. The protective headwear of claim 9, wherein the second force continually increases as the outer shell moves from the first position towards the second position.

11. The protective headwear of claim 1, further comprising a coupling member coupled to and rotatable with the outer shell, wherein the coupling member includes one of the first portion and the second portion of the member.

12. The protective headwear of claim 11, wherein the one of the first portion and the second portion of the member is unitarily formed as one-piece with the coupling member.

13. The protective headwear of claim 12, wherein the other one of the first portion and the second portion is formed separately from the coupling member, and wherein the coupling member and the one of the first portion and the second portion rotate relative to the other one of the first portion and the second portion.

14. The protective headwear of claim 1, wherein the member is a spring.

15. The protective headwear of claim 1, wherein the support member is headgear including at least one strap.

16. The protective headwear of claim 1, wherein the protective headwear is a welding helmet.

17. The protective headwear of claim 10, wherein the second force is provided to the outer shell perpendicular to a side of the outer shell.

18. The protective headwear of claim 10, wherein the outer shell rotates about an axis, and wherein the second force is provided to the outer shell in a direction parallel to the axis.

19. The protective headwear of claim 1 wherein the first bore comprises a first bore side wall which varies in a first bore side wall height around the first bore, and the second bore comprises a second bore side wall which varies in a second bore side wall height around the second bore.

20. The protective headwear of claim 1 further comprising a slider slideably coupled to the support member to adjust a position of the outer shell relative to the support member.

21. The protective headwear of claim 20 further comprising a second actuator coupled to the slider and to the support member, the second actuator to selectively secure and unsecure the slider relative to the support member.

22. The protective headwear of claim 21 further comprising a base rigidly coupled to the slider, the base coupled to the actuator.

23. A protective headwear comprising:
   a support member configured to engage a user's head;
   an outer shell coupled to the support member and rotatable relative to the support member between a first position and a second position; and
   a member coupled between the support member and the outer shell and including a first portion and a second portion, wherein the first portion is thicker near a first end of the first portion and thinner near a second end of the first portion, and wherein the second portion is thicker near a first end of the second portion and thinner near a second end of the second portion, wherein the first and second portions of the member interact to reduce angular velocity of the outer shell as it moves from the first position to the second position; and wherein the first portion comprises a first bore which is asymmetrical and the second portion comprises a second bore which is asymmetrical.

24. The protective headwear of claim 23, wherein the thicker first end of the first portion is adjacent the thinner second end of the second portion with the outer shell in the first position, and wherein the thicker first end of the first portion is adjacent the thicker first end of the second portion with the outer shell in the second position.

25. The protective headwear of claim 23, wherein:

with the outer shell in the first position, the thicker first end of the first portion is adjacent the thinner second end of the second portion and the thinner second end of the first portion is adjacent the thicker first end of the second portion; and with the outer shell in the second position, the thicker first end of the first portion is adjacent the thicker first end of the second portion and the thinner second end of the first portion is adjacent the thinner second end of the second portion.

26. The protective headwear of claim 23, further comprising an actuator, wherein the outer shell is disposed between the actuator and the member.

27. The protective headwear of claim 26, wherein the actuator is moveable relative to the outer shell to apply varying levels of force to the outer shell.

28. A protective headwear comprising:

a support member configured to engage a user's head;

an outer shell coupled to the support member and rotatable relative to the support member between a first position and a second position; and a member coupled between the support member and the outer shell, wherein the member includes a first portion and a second portion formed separately from each other and formed separately from the support member and the outer shell, and wherein the first portion and the second portion are moveable relative to each other as the outer shell moves from the first position to the second position, and wherein the first portion includes a first surface and the second portion includes a second surface, wherein the first surface and the second surface directly engage each other, the first portion comprising a first bore which is asymmetrical and the second portion comprising a second bore which is asymmetrical.

29. The protective headwear of claim 28 further comprising an actuator, wherein the outer shell is disposed between the actuator and the member.

30. The protective headwear of claim 29, wherein the actuator is moveable relative to the outer shell to apply varying levels of force to the outer shell.

* * * * *